United States Patent
Shrestha et al.

(10) Patent No.: US 11,913,060 B1
(45) Date of Patent: Feb. 27, 2024

(54) METHODS FOR QUANTIFYING MIXED-LINKAGE BETA GLUCAN

(71) Applicant: Edeniq, Inc., Visalia, CA (US)

(72) Inventors: Prachand Shrestha, Visalia, CA (US); Denmark Antolin, Visalia, CA (US)

(73) Assignee: Edeniq, Inc., Visalia, CA (US)

( * ) Notice: Subject to any disclaimer, the term of this patent is extended or adjusted under 35 U.S.C. 154(b) by 443 days.

(21) Appl. No.: 16/723,428

(22) Filed: Dec. 20, 2019

Related U.S. Application Data

(60) Provisional application No. 62/783,598, filed on Dec. 21, 2018.

(51) Int. Cl.
 *C12Q 1/54* (2006.01)
 *G01N 1/28* (2006.01)

(52) U.S. Cl.
 CPC .................................. *C12Q 1/54* (2013.01); *G01N 1/28* (2013.01)

(58) Field of Classification Search
 CPC .................................... C12Q 1/54; G01N 1/28
 USPC ............................................................ 435/14
 See application file for complete search history.

(56) References Cited

U.S. PATENT DOCUMENTS

2012/0064574 A1* 3/2012 Tokuyasu .................. C12P 7/10
435/162

OTHER PUBLICATIONS

Baruah et al., Recent Trends in the Pretreatment of Lignocellulosic Biomass for Value-Added Products, Frontiers in Energy Research, vol. 6, Article 141, Published Dec. 18, 2018, pp. 1-19.*

* cited by examiner

*Primary Examiner* — Jennifer M. H. Tichy
(74) *Attorney, Agent, or Firm* — Kilpatrick Townsend & Stockton LLP

(57) ABSTRACT

Methods and solutions are disclosed for the quantification of mixed-linkage beta-glucan in plant biomass samples. Improved alkaline pretreatment, enzymatic hydrolysis, and glucose measurement parameters are provided that increase the accuracy, precision, and sensitivity of mixed-linkage beta-glucan assays.

21 Claims, 3 Drawing Sheets

US 11,913,060 B1

METHODS FOR QUANTIFYING MIXED-LINKAGE BETA GLUCAN

CROSS-REFERENCE TO RELATED APPLICATIONS

This application claims the benefit of priority to U.S. Provisional Patent Application No. 62/783,598 filed Dec. 21, 2018, the contents of which are hereby incorporated by reference herein in their entirety for all purposes.

BACKGROUND

Biofuels produced from agricultural products provide a potential source for new transportation energy. By using such renewable feedstocks as raw materials, it is believed that fuel and other chemicals can be manufactured in a way that is sustainable, economically viable, and environmentally responsible. An example of a first-generation biofuel is ethanol produced from corn. Corn ethanol is made by extracting and converting the starch found in corn kernels into ethanol using readily-available technologies such as enzymatic hydrolyses and fermentations. In developing and operating these processes, it can be valuable to measure and monitor the amount of convertible material present in corn or other plant feedstocks.

One such plant component is mixed-linkage beta-glucan, a non-starch-non-cellulose homopolymer of glucose that is primarily present in the pericarp of cereal grains. This polysaccharide is constituted, in random order, of beta-(1,4) tri- and tetra-saccharides linked by beta-(1,3) linkages. The deconstruction of mixed-linkage beta-glucan can proceed with the use of debranching enzymes, such as lichenase, that cleave the polysaccharide at beta-(1,3) linkages to liberate the beta-(1,4) tri- and tetra-saccharides. These can then be hydrolyzed by beta-glucosidase to produce glucose as a monomer product. Assay protocols and reagents are available for carrying out these reactions to convert some of the mixed-linkage beta-glucan in certain sample types to the more readily measured glucose. While often effective in quantifying high mixed-linkage beta-glucan levels found in plants such as barley and oats, these protocols can have limited accuracy in quantifying lower levels such as those found in corn and other plants.

BRIEF SUMMARY

In general, provided herein are methods that are characterized by the detection of mixed-linkage beta-glucan found in biomass samples. One provided method includes contacting a plant biomass sample with an alkaline mixture, thereby generating a pretreated sample. The alkaline mixture can comprise a metal hydroxide. The concentration of the metal hydroxide in the alkaline mixture can be between 0.2 N and 1 N. The method further includes hydrolyzing the mixed-linkage beta-glucan in the pretreated sample to generate glucose. The method further includes measuring the concentration of glucose in the pretreated sample. The method further includes transforming the measured glucose concentration to a calculated mixed-linkage beta-glucan concentration. In some embodiments, the measuring includes high-performance liquid chromatography.

In some embodiments, the mass ratio of the metal hydroxide to the solids content of the plant biomass sample is between 0.2 and 20. In some embodiments, the metal hydroxide includes sodium hydroxide or potassium hydroxide. In some embodiments, the concentration of the mixed-linkage beta-glucan in the plant biomass sample is between 0 and 2 percent by weight (wt %).

In some embodiments, the contacting is at a pretreatment temperature between 10° C. and 35° C. In some embodiments, the contacting has a pretreatment duration between 20 minutes and 3 hours. In some embodiments, the contacting has a pretreatment pressure within 20% of atmospheric pressure.

In some embodiments, the hydrolyzing includes forming one or more reaction mixtures, wherein each of the one or more reaction mixtures independently includes the pretreated sample and an enzyme. The one or more reaction mixtures can include a first reaction mixture that comprises the pretreated sample and an endo-(1,3)(1,4)-beta-D-glucan 4-glucanohydrolase, and that is formed under conditions suitable for converting the mixed-linkage beta-glucan to oligosaccharides. The one or more reaction mixtures can include a second reaction mixture that comprises the pretreated sample and a beta-glucosidase, and that is formed under conditions suitable for converting the oligosaccharides to glucose.

In some embodiments, the plant biomass sample includes corn. In some embodiments, the plant biomass sample include mash, beer, or distiller's dried grains. In some embodiments, more than 80 wt % of the mixed-linkage beta-glucan in the plant biomass sample is converted to glucose.

Also provided is a solution including a plant biomass sample and a metal hydroxide. The plant biomass sample has a mixed-linkage beta-glucan content between 0 and 2 wt %. The concentration of the metal hydroxide in the solution is between 0.2 N and 1 N. In some embodiments, the mass ratio of the metal hydroxide to the solids content of the plant biomass sample is between 0.2 and 20. In some embodiments, the metal hydroxide includes sodium hydroxide or potassium hydroxide. In some embodiments, the plant biomass sample is from corn. In some embodiments, the plant biomass sample includes mash, beer, or distiller's dried grains.

DETAILED DESCRIPTION

Figure 1:
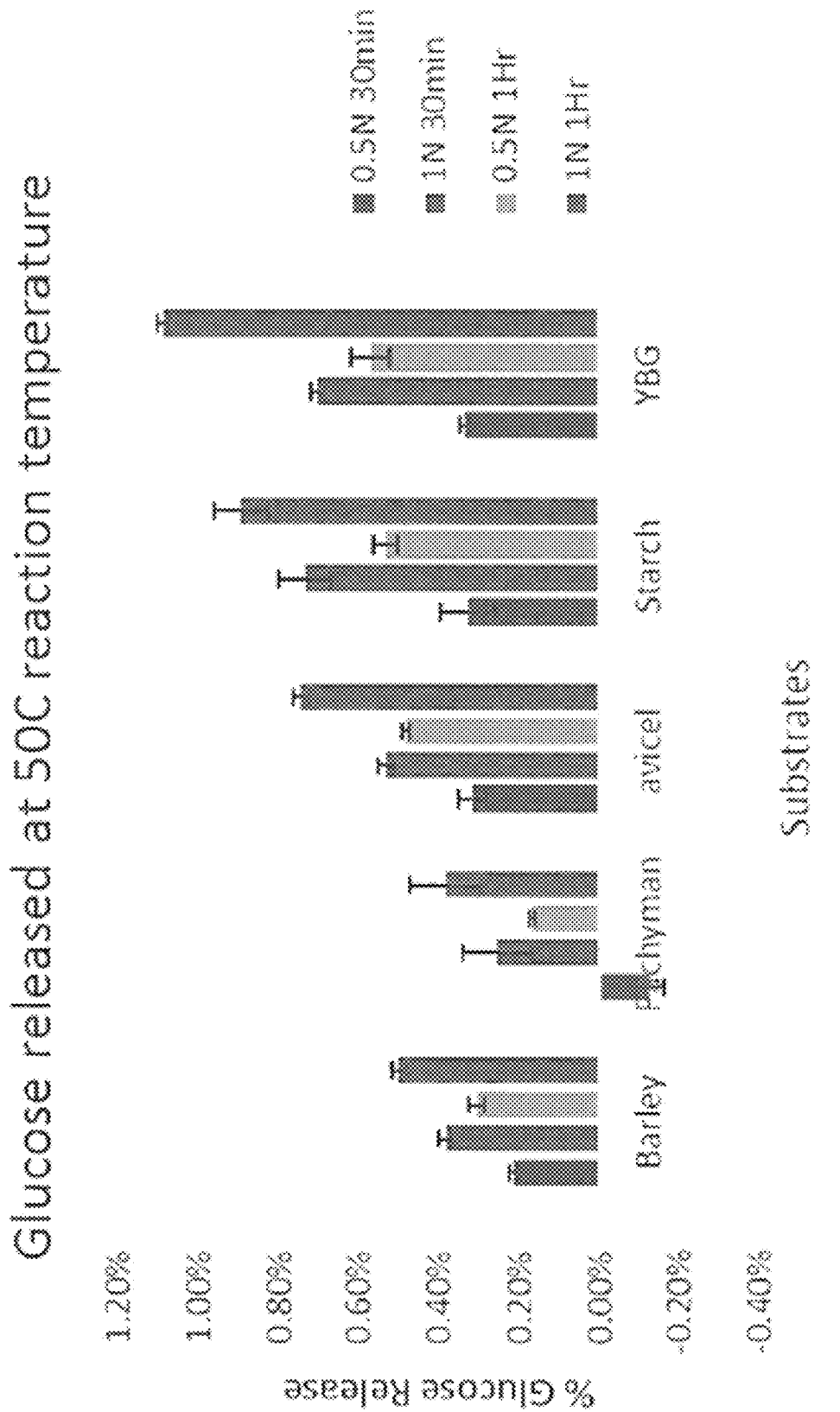
FIG. 1 is a graph of glucose concentrations in biomass samples pretreated with various sodium hydroxide concentrations and pretreatment durations at 50° C.

Some existing procedures have been shown useful in measuring the mixed-linkage beta-glucan content of plant products, such as barley and oats, that generally include approximately 10 wt % or more mixed-linkage beta-glucan on a dry weight basis. Other plants, however, have much lower mixed-linkage beta-glucan levels that can be approximately 2 wt % or less. Among these lower content plants is the important agricultural product, corn. The reduced mixed-linkage beta glucan concentration in corn, coupled with the more limited accessibility of the heteropolysaccharide within the corn kernel, can lead to inconsistent or underreported concentration values when using typical quantification assays. For example, these typical assays use a pretreatment process (e.g., aging for 2 minutes in 20 mM pH 6.5 sodium phosphate buffer at 100° C.) that, while often adequate for solubilizing mixed-linkage beta-glucan in oat or barley, is not strong enough to liberate all of the mixed-linkage beta-glucan tightly held within corn kernels or corn flour. In addition, the commonly used glucose oxidase peroxidase colorimetric measurement technique of these typical assays can lack the sensitivity required to accurately quantify low concentrations of glucose produced from the conversion of low amounts of mixed-linkage beta-glucan.

The inventors have now discovered that by using a particular alkaline treatment of biomass samples, an assay can be surprisingly effective in quantifying the mixed-linkage beta-glucan content of a wide variety of samples. The new assay methods and solutions can be used to accurately determine the mixed-linkage beta-glucan levels in samples that could not be easily measured using previously available assay techniques. For example, an advantage of the provided procedures and compositions is that they can be applied to the accurate determination of lower amounts of biomass mixed-linkage beta-glucan. Such lower amounts are common in plants, such as corn, that are important in the field of renewable biofuels. Examples of corn-based feedstocks for biofuels processes include corn mash, beer, and distiller's dried grains. Another advantage of the methods and solutions disclosed herein is that they have been developed to allow the simultaneous quantitation of mixed-linkage beta-glucan present in both the liquid and the solid phase of a biomass sample.

One provided method includes contacting a plant biomass sample with an alkaline mixture, wherein the alkaline mixture includes a metal hydroxide at a concentration between 0.2 N and 1 N. The contacting of the plant biomass sample with the alkaline mixture generates a pretreated sample. The method further includes hydrolyzing mixed-linkage beta-glucan in the pretreated sample to generate glucose. The concentration of glucose in the pretreated sample is measured, and the measured glucose concentration is transformed to a calculated mixed-linkage beta-glucan concentration.

The calculated mixed-linkage beta-glucan concentration provides compositional information that characterizes the plant biomass sample, and that can be used to guide various processes using the plant biomass as a feedstock. For example, in the brewing industry, the presence of mixed-linkage beta-glucan can negatively impact the performance of wort production, fermentation, and beer filtration steps. Knowledge of the amount of mixed-linkage beta-glucan in a particular brewing feedstock can allow a process to be modified to more effectively break down the complex glucan molecules into smaller units, realizing benefits associated with reduced viscosities, improved product color, higher heat transfers, and other properties. Similarly, in the corn ethanol industry, information about the mixed-linkage beta-glucan concentration in corn-based biomass can be used as an input for guiding process adjustments aimed at enhancing ethanol production efficiency and yield.

In some embodiments, the provide method includes selecting, based on the calculated mixed-linkage beta-glucan concentration, one or more enzymes used to at least partially digest the mixed-linkage beta-glucan in the plant biomass. The enzymes can include, for example, a thermostable alpha-amylase, a glucoamylase, a beta-glucanase, a cellulase, a hemicellulose, a lichenase, or a combination thereof. The enzymes can include one or more heterogenic carbohydrate hydrolyzing enzymes such as amylases, cellulases, beta-glucosidases, cellobiohydrolases, pullulanases, endoglucanases, exoglucanases, xylanases, glucoamylases, inulinases, or others, as well as mixtures or cocktails including any subset of these enzymes or related enzymatic domains. In some embodiments, the method includes selecting, based on the calculated mixed-linkage beta-glucan concentration, the amount of one or more enzymes used to at least partially digest the mixed-linkage beta-glucan in the plant biomass. For example, the calculated mixed-linkage beta-glucan concentration can be used to determine the relative ratio of enzymes in a cocktail mixture used for the digestion of mixed-linkage beta-glucan in the plant biomass. In some embodiments, the method includes selecting, based on the calculated mixed-linkage beta-glucan concentration, a temperature, a pH, or both a temperature and a pH of a "cooking" or treatment step for converting, e.g., enzymatically converting, plant biomass constituents to fermentable sugars.

Plant Biomass Sample

As used herein, the terms "biomass", "biomass feedstock", and "biomass sample" refer to any material comprising cellulosic material, lignocellulosic material, whole grains, starches, inulin, or any other type of structural carbohydrate. Examples of biomass include agricultural products and waste products such as but not limited to grains, e.g., corn, corn kernel fiber, wheat, and barley; sugarcane; corn stover, corn cobs, tubers, Jerusalem artichoke, stalks, and/or other inedible waste parts of food plants; food waste; grasses such as switchgrass, *miscanthus*, and reed canarygrass; and forestry biomass, such as wood, paper, board, and waste wood products. As used herein, the term "lignocellulosic" refers to any material comprising both lignin and cellulose, and optionally also comprising hemicellulose and mixed-linkage plant cell wall beta-glucans. Thus, lignocellulosic materials comprise a subset of cellulosic materials representing those cellulosic materials that also comprise lignin.

The biomass samples described herein can be obtained from cellulosic or lignocellulosic plants such as, but not limited to, grains such as corn and milo (also known as grain sorghum). The samples can be obtained from various stages in a corn ethanol manufacturing process, such as post-liquefied corn mash, samples after fermentation (e.g., beer and distiller's dried grains with solubles (DDGS)), whole stillage, thin stillage, and syrup. In some embodiments, the biomass sample has been subjected to a pretreatment process.

The plant biomass sample is generally provided in a wet state as a sample having a solids content and a water content. The total solids content of the initial cellulosic biomass sample can be measured, for example, according to the Laboratory Analytical Procedure (LAP) of the National Renewable Energy Laboratory (NREL) Technical Report NREL/TP-510-42621. The plant biomass sample can have, for example, a total solids content that is from 5 wt % to 90 wt %, e.g., from 5 wt % to 56 wt %, from 13.5 wt % to 64.5 wt %, from 22 wt % to 73 wt %, from 30.5 wt % to 81.5 wt %, or from 39 wt % to 90 wt %. In terms of upper limits, the plant biomass sample can have a total solids content less than 90 wt %, e.g., less than 81.5 wt %, less than 73 wt %, less than 64.5 wt %, less than 56 wt %, less than 47.5 wt %, less than 39 wt %, less than 30.5 wt %, less than 22 wt %, or less than 13.5 wt %. In terms of lower limits, the plant biomass sample can have a total solids content greater than 5 wt %, e.g., greater than 13.5 wt %, greater than 22 wt %, greater than 30.5 wt %, greater than 39 wt %, greater than 47.5 wt %, greater than 56 wt %, greater than 64.5 wt %, greater than 73 wt %, or greater than 81.5 wt %. Higher solids contents, e.g., greater than 90 wt %, and lower solids contents, e.g., less than 5 wt %, are also contemplated.

In some embodiments, the plant biomass sample is dried prior to addition to the alkaline pretreatment mixture. The biomass sample can be dried using a drying oven. The biomass sample can be dried using a microwave oven. In some embodiments, the biomass sample is dried by lyophilization.

In some embodiments, the plant biomass sample is from corn. The corn-based biomass sample can be from the front or upstream end of a corn processing flow, and can include, for example, corn flour or corn mash. In some embodiments, the plant biomass sample includes flour. In some embodiments, the plant biomass sample includes mash. The corn-based biomass sample can be from the back or downstream end of a corn processing flow, and can include, for example, beer or distiller's dried grains. In some embodiments, the plant biomass sample includes beer. In some embodiments, the plant biomass sample includes distiller's dried grains. In some embodiments, the plant biomass sample includes two or three of mash, beer, and distiller's dried grains.

The concentration of the mixed-linkage beta-glucan in the plant biomass sample can, for example, be between 0 and 2 wt %, e.g., between 0 and 1.2 wt %, between 0.2 wt % and 1.4 wt %, between 0.4 wt % and 1.6 wt %, between 0.6 wt % and 1.8 wt %, or between 0.8 wt % and 2 wt %. In terms of upper limits, the mixed-linkage beta-glucan concentration can be less than 2 wt %, e.g., less than 1.8 wt %, less than 1.6 wt %, less than 1.4 wt %, less than 1.2 wt %, less than 1 wt %, less than 0.8 wt %, less than 0.6 wt %, less than 0.4 wt %, or less than 0.2 wt %. In terms of lower limits, the mixed-linkage beta-glucan concentration can be greater than 0.2 wt %, e.g., greater than 0.4 wt %, greater than 0.6 wt %, greater than 0.8 wt %, greater than 1 wt %, greater than 1.2 wt %, greater than 1.4 wt %, greater than 1.6 wt %, or greater than 1.8 wt %. Higher concentrations, e.g., greater than 2 wt %, are also contemplated.

Pretreatment with Alkaline Mixture

As used here, the term "pretreatment" refers to the treatment of biomass to render the biomass more susceptible to hydrolysis by, for example, saccharification or hydrolysis enzymes. As used herein, the term "pretreated biomass" refers to biomass that has been subjected to pretreatment to render the biomass more susceptible to hydrolysis. The methods and solutions disclosed herein include an alkaline mixture used to pretreat the plant biomass sample. Without being bound by theory, it is believed that this alkaline mixture at least partially degrades the structural rigidity of the plant biomass by, for example, breaking down plant cell walls. This in turn can increase the accessibility of mixed-linkage beta-glucan within the plant biomass to subsequent hydrolysis steps. For example, enzymes used in the hydrolysis can more easily contact the mixed-linkage beta-glucan if the diffusive transport of the enzymes and/or the mixed-linkage beta glucan within the plant biomass sample is increased as a result of the alkaline mixture pretreatment.

The alkaline mixture can include a metal hydroxide. In some embodiments, the metal hydroxide includes sodium hydroxide. In some embodiments, the metal hydroxide is sodium hydroxide. In some embodiments, the metal hydroxide includes potassium hydroxide. In some embodiments, the metal hydroxide is potassium hydroxide. In some embodiments, the metal hydroxide includes sodium hydroxide and potassium hydroxide. In some embodiments, the metal hydroxide consists of sodium hydroxide and potassium hydroxide.

The concentration of the metal hydroxide in the alkaline mixture can be selected to be high enough to release water-soluble mixed-linkage beta-glucan from the plant biomass sample, but not so high as to cause the undesired hydrolysis of other polysaccharides present in the sample. Such nonspecific hydrolysis can cause an increase in glucose concentration unrelated to the amount of mixed-linkage beta-glucan present in the sample, resulting in an overreporting of mixed-linkage beta-glucan content. The metal hydroxide concentration in the alkaline mixture can, for example, be between 0.2 N and 1 N, e.g., between 0.2 N and 0.68 N, between 0.28 N and 0.76 N, between 0.36 N and 0.84 N, between 0.44 N and 0.92 N, or between 0.52 N and 1 N. In terms of upper limits, the metal hydroxide concentration can be less than 1 N, e.g., less than 0.92 N, less than 0.84 N, less than 0.76 N, less than 0.68 N, less than 0.6 N, less than 0.52 N, less than 0.44 N, less than 0.36 N, or less than 0.28 N. In terms of lower limits, the metal hydroxide concentration can be greater than 0.2 N, greater than 0.28 N, greater than 0.36 N, greater than N, greater than 0.52 N, greater than 0.6 N, greater than 0.68 N, greater than 0.76 N, greater than 0.84 N, or greater than 1 N. Higher concentrations, e.g., greater than 1 N, and lower concentrations, e.g., less than 0.2 N, are also contemplated.

The mass ratio of the metal hydroxide to the solids content of the plant biomass sample can, for example, be between 0.2 and 20, e.g., between 0.2 and 3.2, between 0.3 and 5, between 0.5 and 8, between 0.8 and 13, or between 1.3 and 20. In terms of upper limits, the mass ratio of the metal hydroxide to the sample solids content can be less than 20, e.g., less than 13, less than 8, less than 5, less than 3.2, less than 2, less than 1.3, less than 0.8, less than 0.5, or less than 0.3. In terms of lower limits, the mass ratio of the metal hydroxide to the sample solids content can be greater than 0.2, e.g., greater than 0.3, greater than 0.5, greater than 0.8, greater than 1.3, greater than 2, greater than 3.2, greater than 5, greater than 8, or greater than 13. Higher ratios, e.g., greater than 20, and lower ratios, e.g., less than 0.2 are also contemplated.

The contacting of the plant biomass sample with the alkaline solution can occur at a pretreatment temperature selected to be high enough to release water-soluble mixed-linkage beta-glucan from the plant biomass sample, but not so high as to cause the undesired hydrolysis of other polysaccharides present in the sample. The pretreatment temperature can be, for example, between 10° C. and 35° C., e.g., between 10° C. and 25° C., between 12.5° C. and 27.5° C., between 15° C. and 30° C., between 17.5° C. and 32.5° C., or between 20° C. and 35° C. In terms of upper limits, the pretreatment temperature can be less than 35° C., e.g., less than 32.5° C., less than 30° C., less than 27.5° C., less than 25° C., less than 22.5° C., less than 20° C., less than 17.5° C., less than 15° C., or less than 12.5° C. In terms of lower limits, the pretreatment temperature can be greater than 10° C., e.g., greater than 12.5° C., greater than 15° C., greater than 17.5° C., greater than 20° C., greater than 22.5° C., greater than 25° C., greater than 27.5° C., greater than 30° C., or greater than 32.5° C. Higher temperatures, e.g., greater than 35° C., and lower temperatures, e.g., less than 10° C., are also contemplated.

The contacting of the plant biomass sample with the alkaline solution can occur for a pretreatment duration selected to be long enough to release water-soluble mixed-linkage beta-glucan from the plant biomass sample, but not so long as to cause the undesired hydrolysis of other polysaccharides present in the sample. The pretreatment duration can be, for example, between 20 minutes and 3 hours, e.g., between 20 minutes and 116 minutes, between 36 minutes and 132 minutes, between 52 minutes and 148 minutes, between 68 minutes and 164 minutes, or between 84 minutes and 180 minutes. In terms of upper limits, the pretreatment duration can be less than 3 hours, e.g., less than 164 minutes, less than 148 minutes, less than 132 minutes, less than 116 minutes, less than 100 minutes, less than 84 minutes, less than 68 minutes, less than 52 minutes, or less than 36 minutes. In terms of lower limits, the pretreatment duration can be greater than 20 minutes, e.g., greater than 36 minutes, greater than 52 minutes, greater than 68 minutes, greater than 84 minutes, greater than 100 minutes, greater than 116 minutes, greater than 132 minutes, greater than 148 minutes, or greater than 164 minutes. Longer durations, e.g., greater than 3 hours, and shorter durations, e.g., less than 20 minutes, are also contemplated.

The contacting of the plant biomass sample with the alkaline solution can occur at a pretreatment pressure selected to be high enough to release water-soluble mixed-linkage beta-glucan from the plant biomass sample, but not so high as to cause the undesired hydrolysis of other polysaccharides present in the sample. The pretreatment pressure can be, for example, within 20% of atmospheric pressure, e.g. within 18% of atmospheric pressure, within 16% of atmospheric pressure, within 14% of atmospheric pressure, within 12% of atmospheric pressure, within 10% of atmospheric pressure, within 8% of atmospheric pressure, within 6% of atmospheric pressure, within 4% of atmospheric pressure, or within 2% of atmospheric pressure. In some embodiments, the pretreatment pressure is greater than atmospheric pressure. In some embodiments, the pretreatment pressure is less than atmospheric pressure. In some embodiments, the pretreatment pressure is atmospheric pressure.

In some embodiments, the method further includes neutralizing the pretreated solution with the addition of an acid, e.g., an acidic buffer. The acid can include, for example, a metal acetate. In some embodiments, sodium acetate is added to the pretreated solution after the plant biomass sample has been contacted with the alkaline solution for the pretreatment duration. In this way, the pH of the pretreated solution is decreased, ending the pretreatment and limiting the pretreatment duration. Furthermore, the addition of the acid to the pretreated solution can adjust the pH of the pretreated solution to a value that is compatible with subsequent hydrolysis steps. For example, the pH of the pretreated solution can be increased to a value at which a hydrolysis enzyme has a desired activity, stability, or both.

Hydrolysis of Mixed-Linkage Beta-Glucan

As used herein, the term "hydrolysis" refers to the breaking of glycosidic bonds in polysaccharides to yield simple monomeric and/or oligomeric sugars. For example, hydrolysis of cellulose can produce the six-carbon ($C_6$) sugar glucose, whereas hydrolysis of hemicellulose can produce the five-carbon ($C_5$) sugars xylose and arabinose. Hydrolysis can be accomplished by acid treatment or by treatment with enzymes that include, but are not limited to, amylase, cellulase, beta-glucosidase, cellobiohydrolase, pullulanase, endoglucanase, exoglucanase, xylanase, glucoamylase, inulinase, and others, as well as mixtures or cocktails including any subset of these enzymes or related enzymatic domains.

In some embodiments, the hydrolysis of the mixed-linkage beta-glucan in the pretreated sample involves enzymatic hydrolysis. The hydrolysis can include the stepwise formation of one or more reaction mixtures that each independently include the pretreated sample and an enzyme. The hydrolysis can include forming at least one reaction mixture that includes the pretreated sample and two or more enzymes carrying out simultaneous reactions.

In certain aspects, the hydrolysis includes one or more enzymes, e.g., an endo-(1,3)(1,4)-beta-D-glucan 4-glucanohydrolase, that can catalyze the conversion of the mixed-linkage beta-glucan to oligosaccharides. The endo-(1,3)(1,4)-beta-D-glucan 4-glucanohydrolase can be, for example and without limitation, from Clostridium thermocellum or from Bacillus subtilis. In certain aspects, the hydrolysis includes one or more enzymes, e.g., a beta-glucosidase, that can catalyze the conversion of oligosaccharides to glucose. The beta-glucosidase can be, for example and without limitation, from Trichoderma sp., from Aspergillus oryzae, from Trichoderma vixens, from Aspergillus niger, from Agrobacterium sp., from Phanerochaete chrysosporium, or from Thermotoga maritima. In some embodiments, the hydrolyzing of the mixed-linkage beta-glucan in the pretreated sample includes forming a first reaction mixture that comprises endo-(1,3)(1,4)-beta-D-glucan 4-glucanohydrolase, and a second reaction mixture that comprises beta-glucosidase. In some embodiments, the hydrolyzing of the mixed-linkage beta-glucan includes forming a reaction mixture that includes both endo-(1,3)(1,4)-beta-D-glucan 4-glucanohydrolase and beta-glucosidase.

In some embodiments, the method includes forming a first reaction mixture by adding to the pretreated solution endo-(1,3)(1,4)-beta-D-glucan 4-glucanohydrolase at a concentration between 3 U/mL and 40 U/mL, e.g., between 3 U/mL and 14 U/ml, between 3.9 U/mL and 18 U/mL, between 5 U/mL and 24 U/mL, between 6.5 U/mL and 31 U/mL, or between 8.5 U/mL and 40 U/mL. In terms of upper limits, the endo-(1,3)(1,4)-beta-D-glucan 4-glucanohydrolase concentration can be less than 40 U/mL, e.g., less than 31 U/mL, less than 24 U/mL, less than 18 U/mL, less than 14 U/mL, less than 11 U/mL, less than 8.5 U/mL, less than 6.5 U/mL, less than U/mL, or less than 3.9 U/mL. In terms of lower limits, the endo-(1,3)(1,4)-beta-D-glucan 4-glucanohydrolase concentration can be greater than 3 U/mL, e.g., greater than 3.9 U/mL, greater than 5 U/mL, greater than 6.5 U/mL, greater than 8.5 U/mL, greater than 11 U/mL, greater than 14 U/mL, greater than 18 U/mL, greater than 24 U/mL, or greater than 31 U/mL. Higher concentrations, e.g., greater than 40 U/mL, and lower concentrations, e.g., less than 3 U/mL, are also contemplated. As used herein, one unit (U) of endo-(1,3)(1,4)-beta-D-glucan 4-glucanohydrolase activity is defined as the amount of enzyme required to release one μmole of glucose reducing-sugar equivalents per minute from barley β-glucan (10 mg/mL) in sodium phosphate buffer (100 mM), pH 6.5 at 40° C.

In some embodiments, the method includes contacting the pretreated solution and an endo-(1,3)(1,4)-beta-D-glucan 4-glucanohydrolase at a first reaction mixture temperature that is between 40° C. and 60° C., e.g., between 40° C. and 52° C., between 42° C. and 54° C., between 44° C. and 56° C., between 46° C. and 58° C., or between 48° C. and 60° C. In terms of upper limits, the first reaction mixture temperature can be less than 60° C., e.g., less than 58° C., less than 56° C., less than 54° C., less than 52° C., less than 50° C., less than 48° C., less than 46° C., less than 44° C., or less than 42° C. In terms of lower limits, the first reaction mixture temperature can be greater than 40° C., e.g., greater than 42° C., greater than 44° C., greater than 46° C., greater than 48° C., greater than 50° C., greater than 52° C., greater than 54° C., greater than 56° C., or greater than 58° C. Higher temperatures, e.g., greater than 60° C., and lower temperatures, e.g., less than ° C., are also contemplated.

In some embodiments, the method includes contacting the pretreated solution and an endo-(1,3)(1,4)-beta-D-glucan 4-glucanohydrolase at a first reaction mixture pH that is between 3 and 5, e.g., between 3 and 4.2, between 3.2 and 4.4, between 3.4 and 4.6, between 3.6 and 4.8, or between 3.8 and 5. In terms of upper limits, the first reaction mixture pH can be less than 5, e.g., less than 4.8, less than 4.6, less than 4.4, less than 4.2, less than 4, less than 3.8, less than 3.6, less than 3.4, or less than 3.2. In terms of lower limits, the first reaction mixture pH can be greater than 3, e.g., greater than 3.2, greater than 3.4, greater than 3.6, greater than 3.8, greater than 4, greater than 4.2, greater than 4.4, greater than 4.6, or greater than 4.8. Higher pH values, e.g., greater than 5, and lower pH values, e.g., less than 3, are also contemplated.

In some embodiments, the method includes contacting the pretreated solution and an endo-(1,3)(1,4)-beta-D-glucan 4-glucanohydrolase for a first reaction mixture duration that is between 30 minutes and 90 minutes, e.g., between 30 minutes and 66 minutes, between 36 minutes and 77 minutes, between 42 minutes and 78 minutes, between 48 minutes and 84 minutes, or between 54 minutes and 90 minutes. In terms of upper limits, the first reaction mixture duration can be less than 90 minutes, e.g., less than 84 minutes, less than 78 minutes, less than 72 minutes, less than 66 minutes, less than 60 minutes, less than 54 minutes, less than 48 minutes, less than 42 minutes, or less than 36 minutes. In terms of lower limits, the first reaction mixture duration can be greater than 30 minutes, e.g., greater than 36 minutes, greater than 42 minutes, greater than 48 minutes, greater than 54 minutes, greater than 60 minutes, greater than 66 minutes, greater than 72 minutes, greater than 78 minutes, or greater than 84 minutes. Longer durations, e.g., greater than 90 minutes, and smaller durations, e.g., less than 30 minutes, are also contemplated.

In some embodiments, the method includes forming a second reaction mixture by adding to the pretreated solution beta-glucosidase at a concentration between 0.1 U/mL and 1.5 U/mL, e.g., between 0.1 U/mL and 0.94 U/ml, between 0.13 U/mL and 0.67 U/mL, between 0.17 U/mL and 0.87 U/mL, between 0.23 U/mL and 1.14 U/mL, or between 0.3 U/mL and 1.5 U/mL. In terms of upper limits, the beta-glucosidase concentration can be less than 1.5 U/mL, e.g., less than 1.14 U/mL, less than 0.87 U/mL, less than 0.67 U/mL, less than 0.51 U/mL, less than 0.39 U/mL, less than 0.3 U/mL, less than 0.23 U/mL, less than 0.17 U/mL, or less than 0.13 U/mL. In terms of lower limits, the beta-glucosidase concentration can be greater than 0.1 U/mL, e.g., greater than 0.13 U/mL, greater than 0.17 U/mL, greater than 0.23 U/mL, greater than 0.3 U/mL, greater than 0.39 U/mL, greater than 0.51 U/mL, greater than 0.67 U/mL, greater than 0.87 U/mL, or greater than 1.14 U/mL. Higher concentrations, e.g., greater than 1.5 U/mL, and lower concentrations, e.g., less than 0.1 U/mL, are also contemplated. As used herein, one unit (U) of beta-glucosidase activity is defined as the amount of enzyme required to release one µmole of p-nitrophenol from p-nitrophenyl β-glucoside per minute at 40° C. and pH 4.0.

In some embodiments, the method includes contacting the pretreated solution and a beta-glucosidase at a second reaction mixture temperature that is between 40° C. and 60° C., e.g., between 40° C. and 52° C., between 42° C. and 54° C., between 44° C. and 56° C., between 46° C. and 58° C., or between 48° C. and 60° C. In terms of upper limits, the second reaction mixture temperature can be less than 60° C., e.g., less than 58° C., less than 56° C., less than 54° C., less than 52° C., less than 50° C., less than 48° C., less than 46° C., less than 44° C., or less than 42° C. In terms of lower limits, the second reaction mixture temperature can be greater than 40° C., e.g., greater than 42° C., greater than 44° C., greater than 46° C., greater than 48° C., greater than 50° C., greater than 52° C., greater than 54° C., greater than 56° C., or greater than 58° C. Higher temperatures, e.g., greater than 60° C., and lower temperatures, e.g., less than 40° C., are also contemplated.

In some embodiments, the method includes contacting the pretreated solution and a beta-glucosidase at a second reaction mixture pH that is between 3 and 5, e.g., between 3 and 4.2, between 3.2 and 4.4, between 3.4 and 4.6, between 3.6 and 4.8, or between 3.8 and 5. In terms of upper limits, the second reaction mixture pH can be less than 5, e.g., less than 4.8, less than 4.6, less than 4.4, less than 4.2, less than 4, less than 3.8, less than 3.6, less than 3.4, or less than 3.2. In terms of lower limits, the second reaction mixture pH can be greater than 3, e.g., greater than 3.2, greater than 3.4, greater than 3.6, greater than 3.8, greater than 4, greater than 4.2, greater than 4.4, greater than 4.6, or greater than 4.8. Higher pH values, e.g., greater than 5, and lower pH values, e.g., less than 3, are also contemplated.

In some embodiments, the method includes contacting the pretreated solution and a beta-glucosidase for a second reaction mixture duration that is between 30 minutes and 90 minutes, e.g., between 30 minutes and 66 minutes, between 36 minutes and 77 minutes, between 42 minutes and 78 minutes, between 48 minutes and 84 minutes, or between 54 minutes and 90 minutes. In terms of upper limits, the second reaction mixture duration can be less than 90 minutes, e.g., less than 84 minutes, less than 78 minutes, less than 72 minutes, less than 66 minutes, less than 60 minutes, less than 54 minutes, less than 48 minutes, less than 42 minutes, or less than 36 minutes. In terms of lower limits, the second reaction mixture duration can be greater than 30 minutes, e.g., greater than 36 minutes, greater than 42 minutes, greater than 48 minutes, greater than 54 minutes, greater than 60 minutes, greater than 66 minutes, greater than 72 minutes, greater than 78 minutes, or greater than 84 minutes. Longer durations, e.g., greater than 90 minutes, and smaller durations, e.g., less than 30 minutes, are also contemplated.

In some embodiments, the combined efficiency of the hydrolysis and the alkaline pretreatment is such that the majority of the mixed-linkage beta-glucan in the plant biomass sample is converted to glucose. At the maximum theoretical 100 wt % mass conversion of mixed-linkage beta-glucan mass to glucose, the introduction of water molecules via hydrolysis will result in approximately 1.11 grams of glucose formed for every gram of mixed-linkage beta-glucan that is hydrolyzed. The overall mass conversion of the mixed-linkage beta-glucan to glucose can be, for example, between 80 wt % and 100 wt %, e.g., between 80 wt % and 92 wt %, between 82 wt % and 94 wt %, between 84 wt % and 96 wt %, between 86 wt % and 98 wt %, and between 88 wt % and 100 wt %. In terms of lower limits, the conversion of the mixed-linkage beta-glucan to glucose can be greater than 80 wt %, e.g., greater than 82 wt %, greater than 84 wt %, greater than 86 wt %, greater than 88 wt %, greater than 90 wt %, greater than 92 wt %, greater than 94 wt %, greater than 96 wt %, or greater than 98 wt %.

Measurement and Transformation of Glucose Concentration

In some embodiments, the measurement of the glucose concentration in the pretreated sample involves the use of a colorimetric assay, such as the glucose oxidase peroxidase (GOPOD) assay of Megazyme Assay Procedure K-BGLU (2017). In some embodiments, the measurement of the glucose concentration in the pretreated sample involves the use of gas chromatography (GC). A GC measurement technique can, for example, be used to quantify an alditol acetate derivative formed of the glucose present in the pretreated sample. In some embodiments, the measurement of the glucose concentration in the pretreated sample involves the use of high-pressure liquid chromatography (HPLC). Commercial HPLC columns suitable for use with the disclosed method include, for example and without limitation, REZEX™ ROA-Organic Acid H+ and REZEX™ RCM-Monosaccharide Ca+2, available from Phenomenex (Torrance, CA), and AMINEX® HPX-87P, available from Bio-Rad Laboratories (Hercules, CA). The use of GC or HPLC can significantly increase the sensitivity of the detection of glucose, which is advantageous for the accurate quantification of lower concentrations of initial mixed-linkage beta-glucan from which the glucose was produced.

In some embodiments, the method further includes measuring the glucose concentration in one or more negative control samples. The negative control samples can be processed according the other method steps described above, but without the alkaline mixture pretreatment, the enzymatic hydrolysis, or both. An example of a negative control sample is a mixture of the plant biomass sample and water. This negative control sample has not been subjected to either the alkaline mixture pretreatment or the enzymatic hydrolysis, and as a result, any glucose measured in the negative control sample does not originate from mixed-linkage beta-glucan present in the plant biomass sample.

The amount of plant biomass sample in the negative control sample can be identical to the amount of plant biomass sample in the pretreated sample. The volume of water added to the plant biomass sample to form the negative control sample can be identical to the combined volume of the alkaline mixture and enzyme mixtures added to the plant biomass sample to form the pretreated sample. In this way, the concentrations of the plant biomass sample components are diluted to an identical degree in both the pretreated sample and the negative control sample.

In some embodiments, the method further includes measuring the glucose concentration in one or more positive control samples. The positive control samples can include the contents and composition of the pretreated sample, or the negative control sample, with the addition of a spike of a known quantity of a measured compound, e.g., glucose. An example of a positive control sample is a mixture of a plant biomass sample, water, and a predetermined amount of glucose. This positive control sample therefore includes a known amount of glucose in addition to that present in the negative control sample, and a comparison of this known glucose concentration with the glucose concentration reported by the glucose measurement can be used to validate or calibrate the measurement technique. Another example of a positive control sample includes a known quantity of beta-glucan. This type of positive control sample can be subject to the hydrolyses steps described above, converting the mixed-linkage beta-glucan to glucose. The measured glucose concentration for this type of positive control sample can thus be used to confirm that the hydrolysis is generating an expected amount of glucose from an initial known amount of mixed-linkage beta-glucan.

In some embodiments, the method further includes measuring the glucose concentration in the pretreated sample more than once. The glucose concentration in the pretreated sample can be measured, for example, in duplicate, in triplicate, in quadruplicate, in quintuplicate, or more. In some embodiments, the method further includes measuring the glucose concentration in a negative control sample more than once. The glucose concentration in a negative control sample can be measured, for example, in duplicate, in triplicate, in quadruplicate, in quintuplicate, or more. In some embodiments, the method further includes measuring the glucose concentration in a positive control sample more than once. The glucose concentration in a positive control sample can be measured, for example, in duplicate, in triplicate, in quadruplicate, in quintuplicate, or more. The method can include measuring the glucose concentration in a negative control sample, optionally repeatedly, after each 1, 2, 3, 4, 5, 6, 7, 8, 9, 10, or more measurements of the glucose concentration in a pretreated sample. The method can include measuring the glucose concentration in a positive control sample, optionally repeatedly, after each 1, 2, 3, 4, 5, 6, 7, 8, 9, 10, or more measurements of the glucose concentration in a pretreated sample.

In some embodiments, the transformation of the measured glucose concentration value to a calculated mixed-linkage beta-glucan concentration value includes multiplying the measured glucose concentration value by a conversion factor related to the maximum theoretical yield of glucose from mixed-linkage beta glucan. For example, in terms of mass, the conversion factor can be (1.11 g glucose)/(1 g mixed-linkage beta-glucan).

In some embodiments, the transformation of the measured glucose concentration value to a calculated mixed-linkage beta-glucan concentration value includes subtracting a background glucose concentration value from the measured glucose concentration value. This type of transformation can be used when measurements of negative control samples indicate that a nonzero amount of background glucose is present in the original plant biomass sample and not attributable to conversion of mixed-linkage beta-glucan in the pretreatment and hydrolyses steps of the method.

In some embodiments, the transformation of the measured glucose concentration value to the calculated mixed linkage beta-glucan concentration value includes multiplying the measured glucose concentration value by a conversion factor related to an observed or estimated efficiency of the pretreatment and hydrolyses steps of the method. This type of conversion factor can be used when measurements of positive control samples indicate that an incomplete percentage of known beta-glucan is converted to measured glucose in these pretreatment and hydrolyses steps. The estimated yield losses for any of these steps can be based on historical data. The estimated yield losses can be based on one or more controls subjected to identical steps as the sample either at a different time or in parallel with the sample.

Examples

The present invention will be better understood in view of the following non-limiting examples. Any of the operations or materials of the following exemplary methods can be altered as described above to provide another embodiment.

In a series of comparative experiments, three identical samples taken from a single corn flour source were each assayed in triplicate according to existing approaches for measuring mixed-linkage beta-glucan concentration. For each of these nine assays, 100 mg of biomass sample were wetted with 0.2 mL of 50% v/v ethanol in water, and added to 4 mL of a 20 mM pH 6.5 sodium phosphate buffer. The resulting mixture was incubated at 100° C. for 3 minutes, and then cooled to 50° C. for 5 minutes. Lichenase (0.2 mL, 10 U) was added to the treated mixture, which was then aged for 1 hour at 50° C. After this lichenase-catalyzed reaction, 5 mL of a 200 mM pH 4 sodium acetate buffer, and 0.1 mL of beta-glucosidase (0.2 U) in 50 mM pH 4 sodium acetate buffer, were each added. The beta-glucosidase-catalyzed reaction was aged for 10 minutes at 50° C. The glucose in each mixture was then determined, with results shown in Table 1 below.

TABLE 1

Comparative Assay Results

| | β-(1,3)(1,4)-Glucan (wt %) |
|---|---|
| Comparative Example A | −0.15% ± 1.25% |
| Comparative Example B | 0.08% ± 0.01% |
| Comparative Example C | 0.38% ± 0.17% |

It can be seen from the data in Table 1 that although the three comparative samples were each taken from the same source, and thus should include the same mixed-linkage beta-glucan content, the assay measurements of the mixed-linkage beta-glucan concentrations in the samples differed significantly. In addition, the standard deviations from the triplicate measurements of two of the three comparative samples were also higher than desired. These results demonstrate the deficiencies of control approaches for measuring mixed-linkage beta-glucan concentrations, particularly in plant biomass samples, such as corn, having a low mixed-linkage beta glucan content.

Another series of experiments tested the effects of replacing the heated sodium phosphate buffer sample pretreatment of the control method with an alkaline mixture pretreatment. In these tests, plant biomass samples were pretreated with either 2 N potassium hydroxide or 1 N sodium hydroxide. The pretreatments were carried out at either 80° C. or 0° C. prior to quenching by adjusting the mixture pH to 6.5 with the addition of 1.2 N sodium acetate buffer. In all cases the free glucose in related negative control samples not subjected to enzymatic hydrolysis were measured. Results are shown in Table 2 below.

TABLE 2

Comparative Assay Results

| | Alkaline Pretreatment | Free Glucose (wt %) |
|---|---|---|
| Comparative Example D | 2N KOH @ 0° C. | 0.25 |
| Comparative Example E | 2N KOH @ 80° C. | 1.98 |
| Comparative Example F | 1N NaOH @ 80° C. | 2.43 |

From the data in Table 2, in each of these comparative examples the amount of free glucose measured in the absence of enzymatic mixed-linkage beta-glucan hydrolysis is significantly higher than desired. In particular, as the pretreatment temperature is increased to 80° C., the amount of glucose present in the pretreated samples also increases dramatically. These results together indicate that the tested alkaline pretreatments are non-specifically hydrolyzing polysaccharides within the plant biomass samples. This undesired effect then confounds the measurement of mixed-linkage beta-glucan by creating glucose that was not present in the original sample, but which does not necessarily originate from the mixed-linkage beta-glucan being assayed.

The effects of different pretreatment parameters were further tested against a panel of different plant biomass sources. The samples included barley mixed-linkage beta-glucan (Barley), microbial Pachyman beta-(1,3)-glucan (Pachyman), Avicel cellulose beta-(1,4)-glucan (Avicel), starch alpha-(1,4)-glucan (Starch), and yeast beta-(1,3)(1,6)-glucan (YBG). Each source was subjected to triplicate pretreatments at 50° C. using each of four conditions: (1) 0.5 N sodium hydroxide for 30 minutes, (2) 1 N sodium hydroxide for 30 minutes, (3) 0.5 N sodium hydroxide for 1 hour, and (4) 1 N sodium hydroxide for 1 hour. Measurements of free glucose liberated by these pretreatments with no enzyme addition are shown in the graph of FIG. 1. The results demonstrate that at both tested sodium hydroxide concentrations, the 50° C. pretreatment temperature was too high to substantially prevent the release of glucose not related to the presence or concentration of mixed-linkage beta-glucan.

Figure 2:
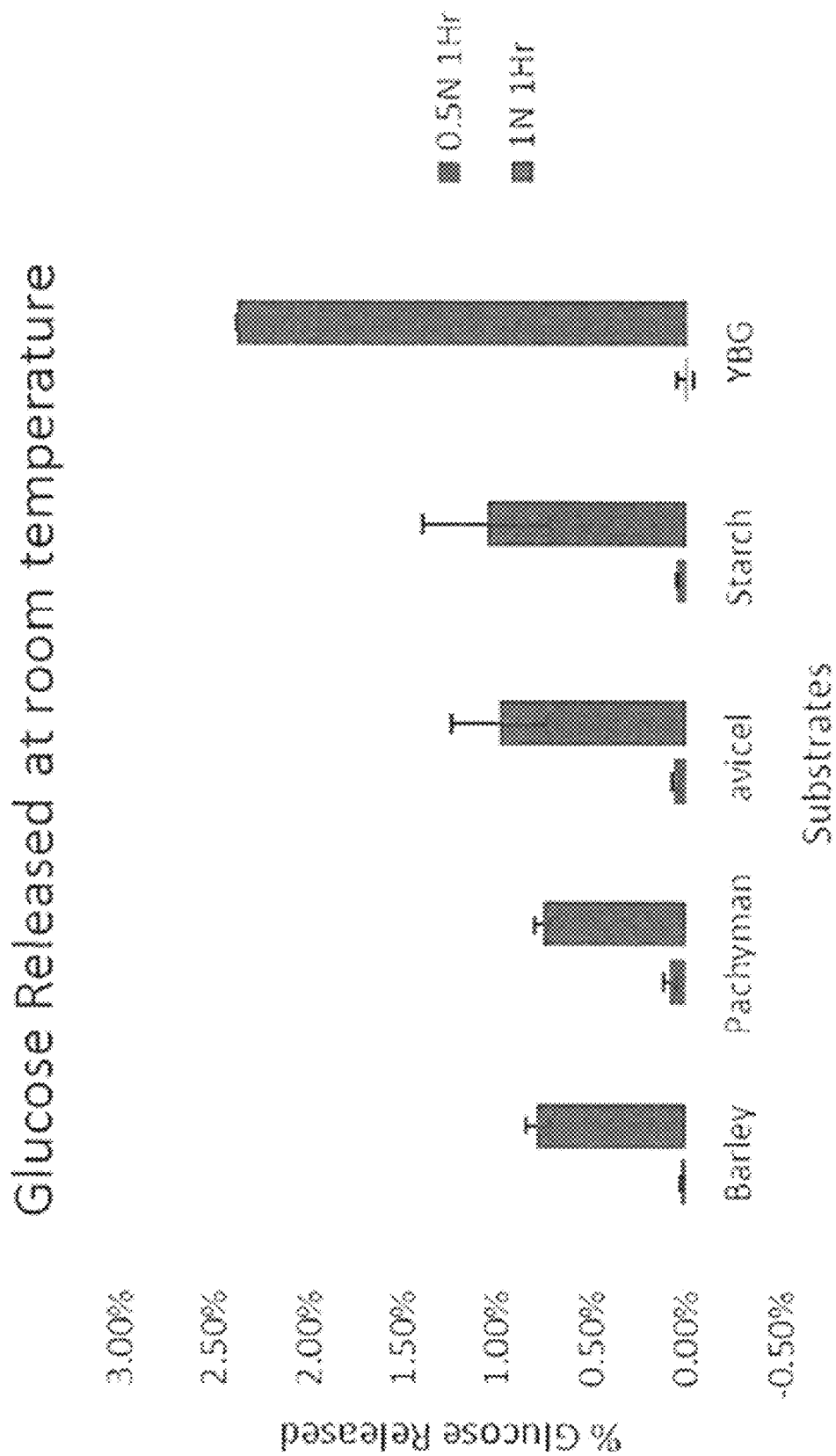
FIG. 2 is a graph of glucose concentrations in biomass samples pretreated with various sodium hydroxide concentrations for 1 hour at room temperature.

The plant biomass panel of FIG. 2 was also tested with pretreatment conditions at room temperature, e.g., between 20° C. and 25° C. In these cases, the sodium hydroxide concentration in the alkaline mixture was either 0.5 N or 1 N, and the pretreatment duration was 1 hour. The resulting free glucose measurements are shown in the graph of FIG. 2. The data demonstrate that alkaline pretreatment of diverse plant biomass samples with 0.5 N sodium hydroxide at room temperature for 1 hour does not cause significant undesired background hydrolysis.

The ability of the provided alkaline pretreatment process to not only reduce background hydrolysis, but to also provide hydrolyzing enzymes with access to the plant biomass sample mixed-linkage beta-glucan, was tested using samples of post-liquefied corn mash. Approximately 250 mg of corn mash was contacted with 2 mL of 0.5 sodium hydroxide and stirred at room temperature for 1 hour. The pretreated sample was then neutralized with 1.1 mL of 1.2 M pH 3.8 sodium acetate buffer. A first enzymatic reaction mixture was formed by combining the pretreated sample and 200 μL of 200 U/mL endo-(1,3)(1,4)-beta-D-glucan 4-glucanohydrolase, and this reaction mixture was aged at 50° C. for 1 hour with mixing every 15 minutes. After this time, a second enzymatic reaction mixture was formed by adding 200 μL of 8 U/mL beta-glucosidase, and this reaction mixture was also aged at 50° C. for 1 hour with mixing every 15 minutes. The resulting mixture was passed through a 25-mm Whatman 0.45 μm filter, and the concentration of glucose in the filtrate was measured.

Figure 3:
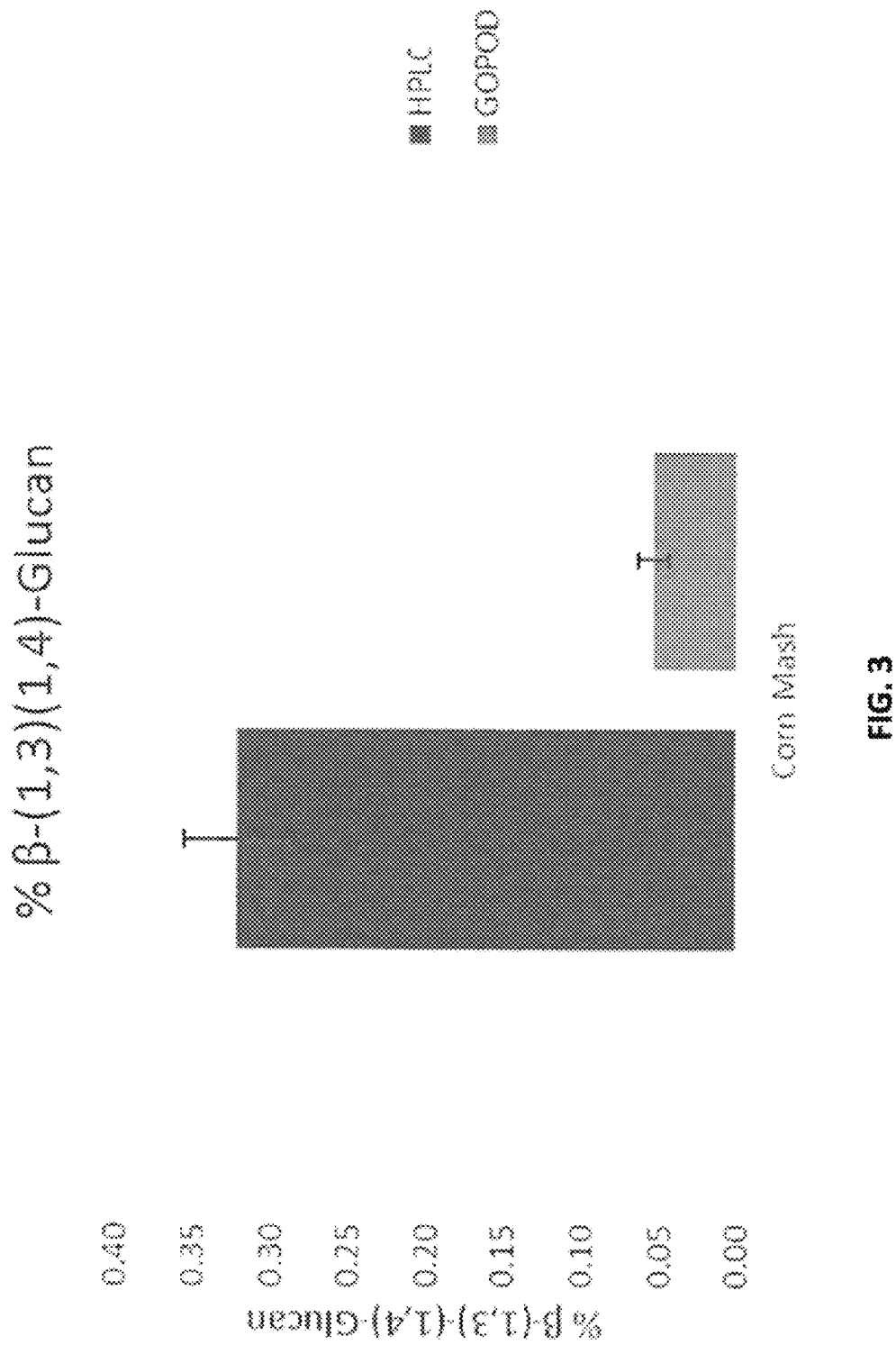
FIG. 3 is a graph of mixed-linkage beta-glucan concentrations calculated from glucose concentration measurements obtained using HPLC or GOPOD techniques.

The graph of FIG. 3 presents data for two different types of measurements of the sample glucose concentration. When the glucose oxidase peroxidase (GOPOD) colorimetric measurement technique is used to provide a glucose concentration measurement, the mixed-linkage beta-glucan level corresponding to this glucose measurement is much lower than that generally reported in literature for this biomass sample type. In contrast, when the hydrolysate sample is measured using a REZEX™ ROA-Organic Acid H+HPLC column using a 0.005 N sulfuric acid mobile phase, the mixed-linkage beta-glucan concentration calculated for the sample is much more consistent with literature values. Additionally, the standard deviations of these values lower than those of the comparative examples of Table 1 above. These findings demonstrate the advantages in precision that can be realized by using the provided methods, and the effectiveness of the pretreatment and measurement steps in allowing for the accurate quantification of mixed-linkage beta-glucan concentrations in diverse plant biomass samples.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications, websites, and databases cited herein are hereby incorporated by reference in their entireties for all purposes. Where a conflict exists between the instant application and a reference provided herein, the instant application shall dominate.

What is claimed is:

1. A method of accurately quantifying a concentration of mixed-linkage beta-glucan in a plant biomass sample, the method comprising:
contacting the plant biomass sample with an alkaline mixture thereby generating a pretreated sample, wherein the alkaline mixture comprises sodium hydroxide or potassium hydroxide at a concentration between 0.2 N and 1 N;
wherein the contacting is at a pretreatment temperature between 10° C. and 35° C. and a pretreatment duration between 20 minutes and less than 3 hours;
hydrolyzing mixed-linkage beta-glucan in the pretreated sample to generate glucose;
measuring the concentration of glucose in the pretreated sample; and
transforming the measured glucose concentration to a calculated mixed-linkage beta-glucan concentration by multiplying the measured glucose concentration value by a conversion factor 1.11 g glucose/1 g mixed-linkage beta-glucan, wherein the calculated mixed-linkage beta-glucan concentration accurately quantifies the concentration of mixed-linkage beta-glucan in the plant biomass sample.

2. The method of claim 1, wherein a mass ratio of the sodium hydroxide or potassium hydroxide to a solids content of the plant biomass sample is between 0.2 and 20.

3. The method of claim 1, wherein the concentration of the mixed-linkage beta-glucan in the plant biomass sample is between 0 and 2 wt %.

4. The method of claim 1, wherein the contacting has a pretreatment pressure within 20% of atmospheric pressure.

5. The method of claim 1, wherein the measuring comprises high-performance liquid chromatography.

6. The method of claim 1, wherein the hydrolyzing comprises forming one or more reaction mixtures, wherein each of the one or more reaction mixtures independently comprises the pretreated sample and an enzyme.

7. The method of claim 6, wherein the hydrolyzing comprises:
forming a first reaction mixture comprising the pretreated sample and an endo-(1,3)(1,4)-beta-D-glucan 4-glucanohydrolase under conditions suitable for converting the mixed-linkage beta-glucan to oligosaccharides; and
forming a second reaction mixture comprising the pretreated sample and a beta-glucosidase under conditions suitable for converting the oligosaccharides to glucose.

8. The method of claim 1, wherein more than 80 wt % of the mixed-linkage beta-glucan in the plant biomass sample is converted to glucose.

9. The method of claim 1, wherein the plant biomass sample is from corn.

10. The method of claim 1, wherein the plant biomass sample comprises mash, beer, or distiller's dried grains.

11. A method of accurately quantifying a concentration of mixed-linkage beta-glucan in a plant biomass sample, the method comprising:
contacting the plant biomass sample with an alkaline mixture thereby generating a pretreated sample, wherein the alkaline mixture comprises a metal hydroxide at a concentration between 0.2 N and 1 N, wherein the contacting is at a pretreatment temperature between 10° C. and 35° C. and a pretreatment duration between 20 minutes and less than 3 hours;
hydrolyzing mixed-linkage beta-glucan in the pretreated sample to generate glucose;
measuring the concentration of glucose in the pretreated sample; and
transforming the measured glucose concentration to a calculated mixed-linkage beta-glucan concentration by multiplying the measured glucose concentration value by a conversion factor 1.11 g glucose/1 g mixed-linkage beta-glucan, wherein the calculated mixed-linkage beta-glucan concentration accurately quantifies the concentration of mixed-linkage beta-glucan in the plant biomass sample.

12. The method of claim 11, wherein the mass ratio of the metal hydroxide to the solids content of the plant biomass sample is between 0.2 and 20.

13. The method of claim 11, wherein the concentration of the mixed-linkage beta-glucan in the plant biomass sample is between 0 and 2 wt %.

14. The method of claim 11, wherein the contacting has a pretreatment pressure within 20% of atmospheric pressure.

15. The method of claim 11, wherein the metal hydroxide comprises sodium hydroxide or potassium hydroxide.

16. The method of claim 11, wherein the measuring comprises high-performance liquid chromatography.

17. The method of claim 11, wherein the hydrolyzing comprises forming one or more reaction mixtures, wherein each of the one or more reaction mixtures independently comprises the pretreated sample and an enzyme.

18. The method of claim 17, wherein the hydrolyzing comprises:
forming a first reaction mixture comprising the pretreated sample and an endo-(1,3)(1,4)-beta-D-glucan 4-glucanohydrolase under conditions suitable for converting the mixed-linkage beta-glucan to oligosaccharides; and
forming a second reaction mixture comprising the pretreated sample and a beta-glucosidase under conditions suitable for converting the oligosaccharides to glucose.

19. The method of claim 11, wherein more than 80 wt % of the mixed-linkage beta-glucan in the plant biomass sample is converted to glucose.

20. The method of claim 11, wherein the plant biomass sample is from corn.

21. The method of claim 11, wherein the plant biomass sample comprises mash, beer, or distiller's dried grains.

* * * * *